United States Patent
Steiner et al.

(10) Patent No.: US 7,833,550 B2
(45) Date of Patent: *Nov. 16, 2010

(54) DRY POWDER FORMULATIONS OF ANTIHISTAMINE FOR NASAL ADMINISTRATION

(75) Inventors: Solomon S. Steiner, Mount Kisco, NY (US); Bryan R. Wilson, Granite Springs, NY (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/842,863

(22) Filed: Aug. 21, 2007

(65) Prior Publication Data

US 2008/0038358 A1 Feb. 14, 2008

Related U.S. Application Data

(63) Continuation of application No. 09/766,362, filed on Jan. 19, 2001.

(60) Provisional application No. 60/176,845, filed on Jan. 19, 2000.

(51) Int. Cl.
*A61K 9/14* (2006.01)
*A61K 9/16* (2006.01)

(52) U.S. Cl. .................. 424/489; 424/490; 424/497

(58) Field of Classification Search .................. None
See application file for complete search history.

(56) References Cited

U.S. PATENT DOCUMENTS

| | | |
|---|---|---|
| 4,151,273 A | 4/1979 | Riegelman et al. |
| 4,272,398 A | 6/1981 | Jaffe |
| 4,332,721 A | 6/1982 | Bernini |
| 4,384,975 A | 5/1983 | Fong |
| 4,861,627 A | 8/1989 | Mathiowitz |
| 5,043,280 A | 8/1991 | Fischer et al. |
| 5,164,194 A | 11/1992 | Hettche |
| 5,352,461 A | 10/1994 | Feldstein et al. |
| 5,354,562 A | 10/1994 | Platz et al. |
| 5,503,852 A * | 4/1996 | Steiner et al. |
| 5,690,954 A * | 11/1997 | Illum |
| 5,700,471 A | 12/1997 | End et al. |
| 5,747,002 A | 5/1998 | Clark et al. |
| 5,776,495 A | 7/1998 | Duclos et al. |
| 5,780,062 A | 7/1998 | Frank et al. |
| 5,800,834 A | 9/1998 | Spireas et al. |
| 5,817,343 A | 10/1998 | Burke |
| 5,833,891 A | 11/1998 | Subramaniam et al. |
| 5,851,453 A | 12/1998 | Hanna et al. |
| 5,855,913 A | 1/1999 | Hanes et al. |
| 5,874,064 A | 2/1999 | Edwards et al. |
| 5,952,008 A | 9/1999 | Backstrom et al. |
| 6,071,497 A | 6/2000 | Steiner et al. |
| 6,136,835 A * | 10/2000 | Camden |

OTHER PUBLICATIONS

Benita, et al., "Characterization of Drug-Loaded Poly(d,l-lactide) Microspheres," *J. Pharm. Sci.* 73:1721-1724 (1984).
Katchalski, et al., "Synthesis of Lysine Anhydride," *J. Amer. Chem. Soc.* 68:879-880 (1946).
Kopple, et al., "A Convenient Synthesis of 2,5-Piperazinediones," *J. Org. Chem.* 33(2):862-864 (1968).
Kornblum, "Sustained-action tablets prepared by employing a spray-drying technique for granulation," *J. Pharm. Sci.* 58(1):125-27 (1969).
Lim, et al., "Microencapsulation of living cells and tissues," *J. Pharm. Sci.* 70:351-354 (1981).
Mathiowitz & Langer, "Polyanhydride Microspheres As Drug Carriers I. Hot-Melt Microencapsulation," *J. Controlled Release* 5:13-22 (1987).
Mathiowitz, et al., "Morphology of Polyanhydride Microsphere Delivery Systems," *Scanning Microscopy* 4:329-340 (1990).
Mathiowitz, et al., "Novel Microcapsules for Delivery Systems," *Reactive Polymers* 6:275-283 (1987).
Mathiowitz, et al., "Polyanhydride Mocrospheres as Drug Carriers. II. Microencapsulation by Solvent Removal," *J. Appl. Polymer Sci.* 35:755-774 (1988).
Mathiowitz, et al., "Polyanydride Microspheres. IV. Morphology and Characterization of Systems Made by Spray Drying," *J. Appl. Polymer Sci.* 45:125-134 (1992).
Salib, et al., "Utilization of Sodium Alginate in Drug Microencapsulation," *Pharmazeutische Industrie* 40(11A):1230 (1978).
Sawhney, et al., "Bioerodible Hydrogels Based on Photopolymerized Poly(ethylene glycol)-co-poly(a-hydroxy acid) Diacrylate Macromers," *Macromolecules* 26:581-587 (1993).

* cited by examiner

*Primary Examiner*—Humera N Sheikh
(74) *Attorney, Agent, or Firm*—K&L Gates LLP; Louis C. Cullman; Michelle Glasky Bergman

(57) ABSTRACT

Dry powder formulations of drugs such as antihistamine for nasal administration are provided where the drug is retained in the nasal cavity, and systemic side effects minimized or eliminated, through the selection of a narrow particle size range, between approximately 10 and 20 microns in diameter. In a preferred embodiment wherein the drug is an antihistamine, retention of the antihistamine at the nasal mucosa is improved and the bitter aftertaste associated with liquid antihistamine formulations significantly reduced. By making a dry powder formulation of an antihistamine (e.g., azelastine) having an average particle size of between 10 and 20 microns, the antihistamine is restricted primarily to the desired target organ, the nasal mucosa. Because the active ingredient stays in the nasal region, a lower dose can be used to achieve the same desired effect. As demonstrated by the examples, this lower dose reduces the incidence of somnolence, and because the active ingredient remains at the target organ and does not accumulate in the back of the throat and mouth, this formulation does not impart a bitter taste.

13 Claims, No Drawings

DRY POWDER FORMULATIONS OF ANTIHISTAMINE FOR NASAL ADMINISTRATION

CROSS-REFERENCE TO RELATED APPLICATIONS

This application is a continuation of U.S. Ser. No. 09/766,362 filed Jan. 19, 2001, entitled "Dry Powder Formulations of Antihistamine for Nasal Administration", by Solomon S. Steiner and Bryan R. Wilson which claims priority to U.S. Ser. No. 60/176,845 filed Jan. 19, 2000.

BACKGROUND OF THE INVENTION

The present invention is generally in the field of pharmaceutical formulations, and more particularly related to methods and compositions for nasally administering antihistamines.

Azelastine hydrochloride is a potent, long acting antihistamine currently administered via the intranasal route in an aqueous solution for the treatment of the symptoms of allergic rhinitis, such as rhinorrhea, sneezing and nasal pruritus. While it is efficacious when administered in this fashion, the liquid nasal spray imparts a long lasting, very bitter taste. Furthermore, somnolence has been reported in some patients taking azelastine. Somnolence is a common unwanted side effect of most antihistamines and is dose related. Azelastine is orally absorbed. Therefore, any azelastine that penetrates the back of the throat and the mouth is orally absorbed, contributing to the central nervous system effects of somnolence and also accounts for the bitter taste experienced by patients.

It would be clearly desirable to have a formulation of azelastine that would not impart a bitter taste and would not produce somnolence.

It is therefore an object of the present invention to provide an antihistamine formulation that does not impart a bitter taste or produce somnolence.

It is another object of the present invention to provide a formulation of antihistamines that provides only local or region effects of the antihistamine, not systemic effects.

SUMMARY OF THE INVENTION

Dry powder formulations of drugs such as antihistamine for nasal administration are provided where the drug is retained in the nasal cavity, and systemic side effects minimized or eliminated, through the selection of a narrow particle size range, between approximately 10 and 20 microns in diameter. In a preferred embodiment wherein the drug is an antihistamine, retention of the antihistamine at the nasal mucosa is improved and the bitter aftertaste associated with liquid antihistamine formulations significantly reduced. By making a dry powder formulation of an antihistamine (e.g., azelastine) having an average particle size of between 10 and 20 microns, the antihistamine is restricted primarily to the desired target organ, the nasal mucosa. Because the active ingredient stays in the nasal region, a lower dose can be used to achieve the same desired effect. As demonstrated by the examples, this lower dose reduces the incidence of somnolence, and because the active ingredient remains at the target organ and does not accumulate in the back of the throat and mouth, this formulation does not impart a bitter taste.

DETAILED DESCRIPTION OF THE INVENTION

Dry powder formulations of antihistamine for nasal administration have been developed which improve retention of the antihistamine at the nasal mucosa without leaving the patient with a bitter aftertaste. A critical aspect is the size range of the particles, between approximately 10 and 20 microns in diameter, which causes the particles to be retained in the nasal region, and not passed into the pulmonary system or mouth. This allows lower dosages to be administered, avoids the systemic side effects such as somnolescence (due to the lower dosage and/or local or regional delivery), and avoids the problem with bitter taste.

I. The Dry Powder Formulation and Methods of Manufacture Thereof

A. Antihistamines

Essentially any antihistamine suitable for delivery to the nasal mucosa can be used in the present formulations. In a preferred embodiment, the antihistamine is azelastine or chlorpheniramine. Other drugs for nasal administration could also be administered instead of the antihistamine. These may include vasoconstrictors and antiinflammatories, and analgesics.

B. Drug Formulation

The antihistamine is formulated as a dry powder consisting primarily of drug or drug and excipient, microparticulate of drug and polymer or material such as diketopiperazine, or microencapsulated drug.

The average size of the particles in the dry powder should be between about 10 and about 20 microns, in order to maximize retention of the particles at the nasal mucosa.

Methods of Making Drug Powder Formulations

The particles constituting the dry powder may be prepared using single and double emulsion solvent evaporation, spray drying, solvent extraction or other methods well known to those of ordinary skill in the art. The particles may be made, for example, using methods for making microspheres or microcapsules known in the art.

Drug particles have been made using a variety of approaches including milling, spray-drying, spray freeze-drying, and supercritical anti-solvent (SAS) precipitation techniques. Various milling techniques are known. For example, see U.S. Pat. No. 5,952,008 to Backstrom et al., U.S. Pat. No. 5,354,562 to Platz et al., and U.S. Pat. No. 5,747,002 to Clark et al. U.S. Pat. No. 4,151,273 to Riegelman et al. discloses a method for preparing a glassy solid matrix of a carrier and a drug, formed at elevated temperature either with or without added solvent. The matrix is rapidly chilled to form a solid mass and ground to a powder for oral administration in a capsule. Methods employing supercritical conditions also are well known. For example, see U.S. Pat. No. 5,043,280 to Fischer et al., U.S. Pat. No. 5,851,453 to Hanna et al., and U.S. Pat. No. 5,833,891 to Subramaniam et al.

Spray drying methods also are well known in the art. For example, U.S. Pat. No. 5,700,471 to End et al. discloses a process for the making fine particles of drug or dye by spray-drying coarse particle dispersions of solutions of the drug. U.S. Pat. No. 5,855,913 to Hanes et al. and U.S. Pat. No. 5,874,064 to Edwards et al. disclose the preparation of aerodynamically light particles between 5 and 30 µm, prepared by spray-drying a therapeutic agent mixed with surfactants or with therapeutic agent mixed with biodegradable polymers. Kornblum, *J. Pharm. Sci.* 58(1):125-27 (1969) discloses spray drying pure drug for purposes of micronization to form spheres in the range of 1-20 µm, and subsequent compression of the spray-dried formulation to produce tablets.

Numerous precipitation techniques are also known. For example, U.S. Pat. No. 5,776,495 to Duclos et al. discloses the formation of solid dispersions created by co-precipitation via drying of at least one therapeutic agent in an organic solvent with a hydrophilic polymer carrier with at least some solubility in the organic solvent. U.S. Pat. No. 4,332,721 to Bernini et al. discloses a process for preparing a spironolactive by precipitation with water from a solution with organic solvents in the temperature range of 0 to 30° C. U.S. Pat. No. 5,800,834 to Spireas et al discloses the use of systems to produce free-flowing powders from liquid lipophilic drugs or from water-insoluble drugs. U.S. Pat. No. 5,780,062 to Frank et al. discloses formation of small particles of organic compounds by precipitation in an aqueous medium containing polymer/amphiphile complexes. U.S. Pat. No. 5,817,343 to Burke discloses a method for forming polymer/drug microparticles by forming a polymer solution/insoluble drug mixture; removing solvent from the mixture to form a hard matrix containing the drug particles in polymer; and micronizing the matrix by fragmenting (e.g., grinding, milling) the matrix below the glass-transition point of the polymer.

Sonication is another technique employed to micronize particles. For example, U.S. Pat. No. 4,384,975 to Fong et al. discloses the preparation of microspheres by solvent removal using sodium oleate as the emulsifier. Micronization of core material by milling or ultrasonic probe sonication of solid drug particles in polymer solution is disclosed.

Examples of water-soluble excipients includes trehalose or lactose. Other excipients can be selected, for example, to aid particle formation, drug release, or site retention, such as with the use of bioadhesive polymers.

Methods of Making Polymeric Drug Formulations

The drug can also be encapsulated or dispersed in a polymeric formulation. Representative polymers which can be used include hydrophilic polymers, such as those containing carboxylic groups, including polyacrylic acid. Bioerodible polymers including polyanhydrides, poly(hydroxy acids) and polyesters, as well as blends and copolymers thereof also can be used. Representative bioerodible poly(hydroxy acids) and copolymers thereof which can be used include poly(lactic acid), poly(glycolic acid), poly(hydroxy-butyric acid), poly(hydroxyvaleric acid), poly(caprolactone), poly(lactide-co-caprolactone), and poly(lactide-co-glycolide). Polymers containing labile bonds, such as polyanhydrides and polyorthoesters. Positively charged hydrogels, such as chitosan, and thermoplastic polymers, such as polystyrene, also can be used. Representative natural polymers which also can be used include proteins, such as zein, modified zein, casein, gelatin, gluten, serum albumin, or collagen, and polysaccharides such as dextrans, polyhyaluronic acid and alginic acid. Representative synthetic polymers include polyphosphazenes, polyamides, polycarbonates, polyacrylamides, polysiloxanes, polyurethanes and copolymers thereof. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt.

Polymers of acrylic and methacrylic acids or esters and copolymers thereof can be used. Representative polymers which can be used include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other polymers which can be used include polyalkylenes such as polyethylene and polypropylene; polyarylalkylenes such as polystyrene; poly(alkylene glycols), such as poly(ethylene glycol); poly(alkylene oxides), such as poly(ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly(vinyl acetate), polyvinyl phenol and polyvinylpyrrolidone. These polymers can be obtained from sources such as Sigma Chemical Co., St. Louis, Mo.; Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

Polymeric microspheres can be fabricated using methods including solvent evaporation, hot-melt microencapsulation and spray drying.

A number of polymers can be used to form the microparticles. As used herein, the term "microparticles" includes microspheres (uniform spheres), microcapsules (having a core and an outer layer of polymer), and particles of irregular shape.

Polymers are preferably biodegradable within the time period over which release is desired or relatively soon thereafter, generally in the range of one year, more typically a few months, even more typically a few days to a few weeks. Biodegradation can refer to either a breakup of the microparticle, that is, dissociation of the polymers forming the microparticles and/or of the polymers themselves. This can occur as a result of change in pH from the carrier in which the particles are administered to the pH at the site of release, as in the case of the diketopiperazines, hydrolysis, as in the case of poly(hydroxy acids), by diffusion of an ion such as calcium out of the microparticle, as in the case of microparticles formed by ionic bonding of a polymer such as alginate, and by enzymatic action, as in the case of many of the polysaccharides and proteins. In some cases linear release may be most useful, although in others a pulse release or "bulk release" may provided more effective results.

Representative synthetic materials are: diketopiperazines, poly(hydroxy acids) such as poly(lactic acid), poly(glycolic acid) and copolymers thereof polyanhydrides, polyesters such as polyorthoesters, polyamides, polycarbonates, polyalkylenes such as polyethylene, polypropylene, poly(ethylene glycol), poly(ethylene oxide), poly(ethylene terephthalate), poly vinyl compounds such as polyvinyl alcohols, polyvinyl ethers, polyvinyl esters, polyvinyl halides, polyvinylpyrrolidone, polyvinylacetate, and poly vinyl chloride, polystyrene, polysiloxanes, polymers of acrylic and methacrylic acids including poly(methyl methacrylate), poly(ethyl methacrylate), poly(butylmethacrylate), poly(isobutyl methacrylate), poly(hexylmethacrylate), poly(isodecyl methacrylate), poly(lauryl methacrylate), polyphenyl methacrylate), poly(methyl acrylate), poly(isopropyl acrylate), poly(isobutyl acrylate), poly(octadecyl acrylate), polyurethanes and co-polymers thereof, celluloses including alkyl cellulose, hydroxyalkyl celluloses, cellulose ethers, cellulose esters, nitro celluloses, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellullose triacetate, and cellulose sulphate sodium salt, poly(butic acid), poly(valeric acid), and poly(lactide-co-caprolactone).

Natural polymers include alginate and other polysaccharides including dextran and cellulose, collagen, albumin and other hydrophilic proteins, zein and other prolamines and hydrophobic proteins, copolymers and mixtures thereof. As used herein, chemical derivatives thereof refer to substitutions, additions of chemical groups, for example, alkyl, alkylene, hydroxylations, oxidations, and other modifications routinely made by those skilled in the art.

Bioadhesive polymers include bioerodible hydrogels described by H. S. Sawhney, C. P. Pathak and J. A. Hubell in *Macromolecules,* 1993, 26, 581-587, polyhyaluronic acids, casein, gelatin, glutin, polyanhydrides, polyacrylic acid, alginate, chitosan, and polyacrylates.

The matrices can be formed of the polymers other than the diketopiperazines by solvent evaporation, spray drying, solvent extraction and other methods known to those skilled in the art. Methods developed for making microspheres for drug delivery are described in the literature, for example, as described by Mathiowitz and Langer, *J. Controlled Release* 5, 13-22 (1987); Mathiowitz, et al., *Reactive Polymers* 6, 275-283 (1987); and Mathiowitz, et al., *J. Appl. Polymer Sci.* 35, 755-774 (1988), the teachings of which are incorporated herein. The selection of the method depends on the polymer selection, the size, external morphology, and crystallinity that is desired, as described, for example, by Mathiowitz, et al., *Scanning Microscopy* 4, 329-340 (1990); Mathiowitz, et al., *J. Appl. Polymer Sci.* 45, 125-134 (1992); and Benita, et al., *J. Pharm. Sci.* 73, 1721-1724 (1984), the teachings of which are incorporated herein.

In solvent evaporation, described for example, in Mathiowitz, et al., (1990), Benita, and U.S. Pat. No. 4,272,398 to Jaffe, the polymer is dissolved in a volatile organic solvent. The drug, either in soluble form or dispersed as fine particles, is added to the polymer solution, and the mixture is suspended in an aqueous phase that contains a surface active agent such as poly(vinyl alcohol). The resulting emulsion is stirred until most of the organic solvent evaporates, leaving solid microspheres.

In general, the polymer can be dissolved in methylene chloride. Several different polymer concentrations can be used, for example, between 0.05 and 0.20 g/ml. After loading the solution with drug, the solution is suspended in 200 ml of vigorously stirring distilled water containing 1% (w/v) poly (vinyl alcohol) (Sigma Chemical Co., St. Louis, Mo.). After four hours of stirring, the organic solvent will have evaporated from the polymer, and the resulting microspheres will be washed with water and dried overnight in a lyophilizer.

Microspheres with different sizes (1-1000 microns) and morphologies can be obtained by this method which is useful for relatively stable polymers such as polyesters and polystyrene. However, labile polymers such as polyanhydrides may degrade due to exposure to water. For these polymers, hot melt encapsulation and solvent removal may be preferred.

In hot melt encapsulation, the polymer is first melted and then mixed with the solid particles of DNA, preferably sieved to less than 50 µm. The mixture is suspended in a non-miscible solvent such as silicon oil and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with diameters between one and 1000 microns can be obtained with this method. The external surface of spheres prepared with this technique are usually smooth and dense. This procedure is useful with water labile polymers, but is limited to use with polymers with molecular weights between 1000 and 50000.

Solvent removal was primarily designed for use with polyanhydrides. In this method, the drug is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike solvent evaporation, this method can be used to make microspheres from polymers with high melting points and a wide range of molecular weights. Microspheres having a diameter between one and 300 microns can be obtained with this procedure. The external morphology of the spheres is highly dependent on the type of polymer used.

In spray drying, the polymer is dissolved in an organic solvent such as methylene chloride (0.04 g/ml). A known amount of active drug is suspended (if insoluble) or co-dissolved (if soluble) in the polymer solution. The solution or the dispersion is then spray-dried. Typical process parameters for a mini-spray drier are as follows: polymer concentration=0.04 g/ml, inlet temperature=24° C., outlet temperature=13 to 15° C., aspirator setting=15, pump setting=10 ml/min, spray flow=600 NLh$^{-1}$, and nozzle diameter=0.5 mm. Microspheres ranging in diameter between one and ten microns can be obtained with a morphology which depends on the selection of polymer.

Double walled microspheres can be prepared according to U.S. Pat. No. 4,861,627 to Mathiowitz.

Hydrogel microspheres made of gel-type polymers such as alginate or polyphosphazines or other dicarboxylic polymers can be prepared by dissolving the polymer in an aqueous solution, suspending the material to be incorporated into the mixture, and extruding the polymer mixture through a microdroplet forming device, equipped with a nitrogen gas jet. The resulting microspheres fall into a slowly stirring, ionic hardening bath, as described, for example, by Salib, et al., *Pharmazeutische Industrie* 40-11A, 1230 (1978), the teachings of which are incorporated herein. The advantage of this system is the ability to further modify the surface of the microspheres by coating them with polycationic polymers such as polylysine, after fabrication, for example, as described by Lim, et al., *J. Pharm. Sci.* 70, 351-354 (1981). For example, in the case of alginate, a hydrogel can be formed by ionically crosslinking the alginate with calcium ions, then crosslinking the outer surface of the microparticle with a polycation such as polylysine, after fabrication. The microsphere particle size will be controlled using various size extruders, polymer flow rates and gas flow rates.

Chitosan microspheres can be prepared by dissolving the polymer in acidic solution and crosslinking with tripolyphosphate. For example, carboxymethylcellulose (CMC) microsphere are prepared by dissolving the polymer in an acid solution and precipitating the microspheres with lead ions. Alginate/polyethylene imide (PEI) can be prepared to reduce the amount of carboxyl groups on the alginate microcapsules.

Methods for Forming Diketopiperazine Microparticles

Methods for making diketopiperazine microparticles are described in U.S. Pat. Nos. 5,352,461, 5,503,852, and 6,071,497, the teachings of which are incorporated herein.

A system based upon diketopiperazine structural elements or one of its substitution derivatives, including diketomorpholihes, diketodioxanes or others, forms microparticles with desirable size distributions and pH ranges as well as good cargo tolerance. A wide range of stable, reproducible characteristics can be generated with appropriate manipulations of the attachment sites, resulting in substantial yields and excellent reproducibility.

The diketopiperazines or their substitution analogs are rigid planar rings with at least six ring atoms containing heteroatoms and unbonded electron pairs. One or both of the nitrogens can be replaced with oxygen to create the substitution analogs diketomorpholine and diketodioxane, respectively. Although it is possible to replace a nitrogen with a sulfur atom, this does not yield a stable structure.

Diketopiperazines can be formed by cyclodimerization of amino acid ester derivatives, as described by Katchalski, et al, *J. Amer. Chem. Soc.* 68, 879-880 (1946), by cyclization of dipeptide ester derivatives, or by thermal dehydration of amino acid derivatives in high-boiling solvents; as described by Kopple, et al., *J. Org. Chem.* 33(2), 862-864 (1968), the teachings of which are incorporated herein. 2,5-diketo-3,6-di(aminobutyl)piperazine (Katchalski et al. refer to this as lysine anhydride) was prepared via cyclodimerization of N-epsilon-P-L-lysine in molten phenol, similar to the Kopple method in *J. Org. Chem.*, followed by removal of the blocking (P)-groups with 4.3 M HBr in acetic acid. This route is preferred because it uses a commercially available starting material, it involves reaction conditions that are reported to preserve stereochemistry of the starting materials in the product and all steps can be easily scaled up for manufacture.

Diketomorpholine and diketooxetane derivatives can be prepared by stepwise cyclization in a manner similar to that disclosed in Katchalski, et al, *J. Amer. Chem. Soc.* 68, 879-880 (1946).

The diketopiperazine derivatives are symmetrical when both side chains are identical. The side chains can contain acidic groups, basic groups, or combinations thereof. Other preferred compounds can be obtained by replacing the succinyl group(s) in the above compound with glutaryl, maleyl or fumaryl groups.

Drug can be encapsulated within microparticles by dissolving a diketopiperazine with acidic side chains in bicarbonate or other basic solution, adding the drug in solution or suspension to be encapsulated, then precipitating the microparticle by adding acid, such as 1 M citric acid. In another embodiment, drug can be encapsulated within microparticles by dissolving a diketopiperazine with basic side chains in an acidic solution, such as 1 M citric acid, adding the drug in solution or suspension to be encapsulated, then precipitating the microparticle by adding bicarbonate or other basic solution. In a third embodiment, drug is encapsulated within microparticles by dissolving a diketopiperazine with both acidic and basic side chains in an acidic or basic solution, adding the drug in solution or suspension to be encapsulated, then precipitating the microparticle by neutralizing the solution.

The microparticles can be stored in the dried state and suspended for administration to a patient. In the first embodiment, the reconstituted microparticles maintain their stability in an acidic medium and dissociate as the medium approaches physiological pH in the range of between 6 and 14. In the second embodiment, suspended microparticles maintain their stability in a basic medium and dissociate at a pH1 of between 0 and 6. In the third embodiment, the reconstituted microparticles maintain their stability in an acidic or basic medium and dissociate as the medium approaches physiological pH in the range of pH between 6 and 8.

II. Devices and Methods for Dispensing Doses of the Dry Powder

The dry powder formulation can be administered by the use of a nasal insulator. The insulator produces a finely divided cloud of the dry powder. The insufflator preferably is provided with means to ensure administration of a substantially fixed amount of the composition. The powder may be used directly with an insufflator which is provided with a bottle or container for the powder, or the powder may be filled into a capsule or cartridge, such as a gelatin capsule, or other single dose device adapted for nasal administration. The insufflator preferably has means to open the capsule or other dose device.

The present invention will be further understood with reference to the following non-limiting examples.

EXAMPLE 1

Azelastine Dry Powder Formulation No. 1

One gram of azelastine HCT was dissolved in 118 ml $H_2O$ to form a uniform clear solution. The solution was then pumped through an Ultrasonic Homogenizer into a 125×60 Pyrex crystallization dish containing liquid $N_2$. The pump flow was 8 ml/min, and the ultrasonic power supply output was set at 90 units. The sample was held at −80° C. until lyophilization.

Lyophilization Process:

| |
|---|
| 24 hours at 15° C. |
| 24 hours at 25° C. |
| 20 hours at 45° C. |

The sample lost 4.38% of its original weight on drying. Using a Malvern Instrument laser light scattering device, particle size was measured as a dry powder.

Particle Size in Microns:

| 10% | 50% | 90% | vol. mean | mode | sauter mean |
|---|---|---|---|---|---|
| 3.15 | 12.23 | 32.20 | 19.56 | 14.63 | 6.92 |

EXAMPLE 2

Azelastine Dry Powder Formulation No. 2

To a solution of 1 g Azelastine HCI in 100 ml $H_2O$, 1 g lactose in 18 ml of $H_2O$ was added. The resulting uniform clear solution was then pumped through an Ultrasonic Homogenizer into a 125×60 Pyrex crystallization dish containing liquid $N_2$. The pump flow was 8 ml/min, and the ultrasonic power supply output was set at 90 units. The sample was held at −80° C. until lyophilization.

Lyophilization Process:

| |
|---|
| 24 hours at 15° C. |
| 24 hours at 25° C. |
| 20 hours at 45° C. |

The sample lost 3.35% of its original weight on drying. Using a Malvern Instrument laser light scattering device, particle size was measured as a dry powder.

Particle Size in Microns:

| 10% | 50% | 90% | vol. mean | mode | sauter mean |
|---|---|---|---|---|---|
| 2.99 | 10.77 | 43.52 | 22.10 | 11.32 | 6.74 |

EXAMPLE 3

Testing of Azelastine Dry Powder Formulation Nos. 1 and 2 vs. Liquid Nasal Spray Azelastine Procedure Number 3 gelatin capsules were filled with 0.29 mg/capsule of Formulation No. 1 or 0.57 mg/capsule of Formulation No. 2. Both formulations and commercially available liquid nasal spray azelastine, (ASTELIN™, Wallace Laboratories) were administered, in random order to three volunteer subjects suffering from seasonal allergic rhinitis, on four separate occasions, (liquid nasal spray 2×, Formulation 1, 1× and Formulation 2, 1×). Volunteers were administered one capsule to each nostril on each test occasion of the dry powder formulation and two sprays per nostril on each test occasion of the liquid formulation. This regimen of dosing equated dose of active drug, (azelastine) administered across all test conditions.

Volunteers were questioned as to their experience of taste, after-taste, efficacy and alertness, immediately, 15 minutes, 30 minutes, 1 hour, 2 hours, 4 hours, and 24 hours after administration of the drug.

Results and Conclusions:

All three volunteers, on both occasions, complained of a bitter taste and after taste when administered the liquid formulation; immediately and at 15 minutes. One volunteer complained of a bitter aftertaste at 30 minutes on one of her two tests with the liquid formulation. In contrast, only one volunteer, on one occasion could detect any taste whatsoever when administered either dry powder formulation, and then only immediately after administration. She described this as a very mild experience compared to the liquid formulation. All volunteers, in all conditions, judged the treatments to be efficacious in relieving rhinorrhea and sneezing. There were no incidences of somnolence or reduction in alertness in any condition.

These dry powder formulations were effective in entirely preventing or markedly reducing the bitter taste and aftertaste associated with the currently used liquid nasal spray of azelastine.

EXAMPLE 4

Chlorpheniramine Dry Powder Formulation

Dry powder formulations of chlorpheniramine, a common antihistamine, were made and tested with similar good results as in the examples above. As most antihistamines are very bitter, this approach and the formulations described herein seem broadly applicable to nasally delivering a variety of antihistamines or other drugs.

EXAMPLE 5

Diketopiperazine Antihistamine Formulation

Antihistamine was also formulated in diketopiperazine. Diketopiperazine particles (10 to 20 microns in diameter) were suspended in aqueous medium. Antihistamine was added, the suspension acidified, and the suspension lyophilized to yield antihistamine powder.

Results of administration to volunteers were similar to the results obtained in examples 1-4.

Modifications and variations of the present invention will be obvious to those of skill in the art from the foregoing detailed description. Such modifications and variations are intended to come within the scope of the following claims.

We claim:

1. A composition for the nasal administration of a drug to a patient comprising a drug in a dry powder form in a dosage formulation suitable for administration to the nasal mucosa, the dry powder made by a process comprising the following steps:
   providing preformed diketopiperazine microparticles between 10 and 20 microns in diameter;
   suspending said diketopiperazine microparticles in an aqueous medium with a drug to form a suspension; and
   forming drug-coated diketopiperazine microparticles by removing solvent from said suspension,
   wherein said drug-coated diketopiperazine microparticles are between about 10 and about 20 microns in diameter, more than 50% of the particles have a size greater than about 10 microns, and wherein said particles are maximally retained in the nasal cavity.

2. The composition of claim 1 wherein the drug is selected from the group consisting of antihistamines, vasoconstrictors, antiinflammatories and analgesics.

3. The composition of claim 2 wherein the antihistamine is selected from the group consisting of chlorpheniramine and azelastine.

4. The composition of claim 1 wherein the drug is formulated in a polymeric carrier.

5. A drug delivery device for nasal administration comprising:
   a drug in a dry powder form comprising diketopiperazine microparticles coated with said drug wherein said drug-coated diketopiperazine microparticles have an average particle size of between about 10 and about 20 microns in diameter, more than 50% of the particles have a size greater than about 10 microns, and wherein said particles are maximally retained in the nasal cavity; and
   a device for delivering a measured dose of the drug to the nasal mucosa.

6. The device of claim 5 wherein the device is a nasal insufflator.

7. The device of claim 5 wherein the drug is selected from the group consisting of antihistamines, vasoconstrictors, antiinflammatories and analgesics.

8. The device of claim 7 wherein the antihistamine is selected from the group consisting of chlorpheniramine and azelastine.

9. The device of claim 5 wherein the drug is formulated in a polymeric carrier.

10. A method of administering a drug to the nasal mucosa of a patient in need thereof, comprising
   nasally administering the dry powder drug-coated diketopiperazine microparticles of claim 1 in a dosage formulation suitable for nasal administration wherein said particles are maximally retained in the nasal cavity and said drug does not impart a bitter aftertaste in said patient.

11. The method of claim 10 wherein the drug is selected from the group consisting of antihistamines, vasoconstrictors, antiinflammatories and analgesics.

12. The method of claim 11 wherein the antihistamine is selected from the group consisting of chlorpheniramine and azelastine.

13. The method of claim 10 wherein the drug is formulated in a polymeric carrier.

* * * * *